United States Patent
Lee et al.

(10) Patent No.: US 9,846,127 B2
(45) Date of Patent: Dec. 19, 2017

(54) COLORIMETRIC DETECTION SENSOR AND COLORIMETRIC DETECTION METHOD FOR DETECTING CYANIDE ANION BY ETCHING OF GOLD NANORODS

(71) Applicant: KOREA INSTITUTE OF SCIENCE AND TECHNOLOGY, Seoul (KR)

(72) Inventors: Kangbong Lee, Seoul (KR); Yunsik Nam, Seoul (KR); Sujin Lee, Seoul (KR); Yeonhee Lee, Seoul (KR); Inhwan Oh, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/357,169

(22) Filed: Nov. 21, 2016

(65) Prior Publication Data

US 2017/0160205 A1 Jun. 8, 2017

(30) Foreign Application Priority Data

Dec. 2, 2015 (KR) .......................... 10-2015-0170887

(51) Int. Cl.
*G01N 21/80* (2006.01)
*G01N 21/25* (2006.01)
(Continued)

(52) U.S. Cl.
CPC ............ *G01N 21/80* (2013.01); *G01N 21/251* (2013.01); *G01N 21/78* (2013.01); *G01N 31/22* (2013.01);
(Continued)

(58) Field of Classification Search
CPC ...... G01N 21/78; G01N 27/12; G01N 27/126; G01N 31/224; G01N 33/4925;
(Continued)

(56) References Cited

U.S. PATENT DOCUMENTS 8,497,131 B2 * 7/2013 Natan .................... B22F 1/0025
436/166
2005/0037514 A1 * 2/2005 Carron ................. G01N 21/658
436/171
(Continued)

FOREIGN PATENT DOCUMENTS

KR 10-2010-0113388 A 10/2010
KR 10-2012-0053405 A 5/2012
(Continued)

OTHER PUBLICATIONS

US EPA, Titrimetric and manual spectrophotometric determinative methods for cyanide, Method 9014, Dec. 1996, pp. 9214-1-9124-7.
(Continued)

*Primary Examiner* — Jennifer Wecker
(74) *Attorney, Agent, or Firm* — Goldilocks Zone IP Law (57) ABSTRACT

Disclosed are a colorimetric detection sensor and colorimetric detection method of a cyanide anion ($CN^-$) by etching of gold nanorods. The colorimetric detection sensor and colorimetric detection method use label-free nanorods having no modifier attached to a surface of gold nanorods (AuNRs), wherein the aspect ratio of nanorods, pH condition and/or amount of a surfactant are controlled to carry out selective etching and to cause a change in color only by $CN^-$ so that $CN^-$ contained or dissolved in poison, water-contaminated environmental samples and legal evidence samples may be detected with ease, and show excellent selectivity, sensitivity and quantitative analyzability to $CN^-$ to provide high usefulness.

13 Claims, 13 Drawing Sheets

(51) Int. Cl.
  *G01N 21/78* (2006.01)
  *G01N 31/22* (2006.01)
  *G01N 33/52* (2006.01)
  *G01N 33/84* (2006.01)
  *G01N 27/12* (2006.01)
  *G01N 33/50* (2006.01)
  *G01N 33/53* (2006.01)
  *G01N 33/49* (2006.01)
  *B82Y 30/00* (2011.01)

(52) U.S. Cl.
  CPC .......... *G01N 31/224* (2013.01); *G01N 33/84* (2013.01); *B82Y 30/00* (2013.01); *G01N 27/12* (2013.01); *G01N 27/126* (2013.01); *G01N 33/4925* (2013.01); *G01N 33/5014* (2013.01); *G01N 33/5308* (2013.01); *Y10T 436/172307* (2015.01)

(58) Field of Classification Search
  CPC .......... G01N 33/5014; G01N 33/5308; G01N 33/84; Y10T 436/172307
  See application file for complete search history.

(56) References Cited

U.S. PATENT DOCUMENTS

| | | | |
|---|---|---|---|
| 2005/0130240 A1* | 6/2005 | Lin | B82Y 5/00 435/7.32 |
| 2011/0109902 A1* | 5/2011 | Lin | G01N 21/658 356/301 |
| 2011/0183140 A1* | 7/2011 | Fourkas | B82Y 5/00 428/378 |
| 2011/0236992 A1* | 9/2011 | Lee | B82Y 15/00 436/501 |
| 2013/0344620 A1* | 12/2013 | O'Farrell | G01N 21/78 436/501 |
| 2015/0037900 A1 | 2/2015 | Rella | |
| 2015/0038578 A1* | 2/2015 | Nikoobakht | A61K 41/0052 514/495 |
| 2016/0131622 A1* | 5/2016 | Akbari Khorami | G01N 31/228 436/135 |

FOREIGN PATENT DOCUMENTS

| | | |
|---|---|---|
| KR | 10-1183956 B1 | 9/2012 |
| KR | 10-1195377 B1 | 10/2012 |
| KR | 10-1271418 B1 | 6/2013 |

OTHER PUBLICATIONS

US EPA, Potentiometric determination of cyanide in aqueous samples and distillates with ion-selective electrode, Method 9213, Dec. 1996, pp. 9213-1-9213-8.

US EPA, Available cyanide by flow injection, ligand exchange and amperometry, Method OIA-1677, Jan. 2004, pp. 1-26.

Huanjun Chen et al., Gold nanorods and their plasmonic properties, The Royal Society of Chemistry 2013, Nov. 6, 2012, pp. 2679-2724, Chem., Soc. Rev., vol. 42.

Fei-Ming Li et al., Non-aggregation based label free colorimetric sensor for the detection of Cr (VI) based on selective etching of gold nanorods, Sensors and Actuators B, Feb. 2, 2011, pp. 817-822, vol. 155.

Yingshuai Liu et al., Polyamine-capped gold nanorod as a localized surface Plasmon resonance probe for rapid and sensitive copper(II) ion detection, Journal of Colloid and Interface Science, Oct. 23, 2014, pp. 7-11, vol. 439.

Emily C. Heider et al., Portable mercury sensor for tap water using surface plasmon resonance of immobilized gold nanorods, Talanta, May 26, 2012, pp. 180-185, vol. 99.

Jie Cao et al., Effective surface modification of gold nanorods for localized surface plasmon resonance-based biosensors, Sensors and Actuators B, May 14, 2012, pp. 360-367, vol. 169.

Arpad Jakab et al., Highly Sensitive Plasmonic Silver Nanorods, ACS Nano, Aug. 18, 2011, pp. 6880-6885, vol. 5, No. 9.

Jie Cao et al., Gold nanorod-based localized surface plasmon resonance biosensors: A review, Sensors and Actuators B., Jan. 25, 2014, pp. 332-351, vol. 195.

Liu et al., Gold-Nanocluster-Based Fluorescent Sensors for Highly Sensitive and Selective Detection of Cyanide in Water, Advanced Functional Materials, Feb. 22, 2010, pp. 951-956, vol. 20.

Chen et al., Highly sensitive label-free colorimetiric sensing of nitrite based on etching of gold nanorods, Analyst, Sep. 3, 2012, pp. 5197-5200, vol. 137.

\* cited by examiner

COLORIMETRIC DETECTION SENSOR AND COLORIMETRIC DETECTION METHOD FOR DETECTING CYANIDE ANION BY ETCHING OF GOLD NANORODS

CROSS-REFERENCE TO RELATED APPLICATION

This application claims priority to Korean Patent Application No. 10-2015-0170887, filed on Dec. 2, 2015, and all the benefits accruing therefrom under 35 U.S.C. §119, the contents of which in its entirety are herein incorporated by reference.

BACKGROUND

1. Field

The present disclosure relates to a colorimetric detection sensor and a colorimetric detection method of a cyanide anion ($CN^-$) based on etching of gold nanorods.

More particularly, the present disclosure relates to a colorimetric detection sensor and a colorimetric detection method, which use label-free nanorods having no modifier attached to the surface of gold nanorods (AuNRs), wherein the aspect ratio of nanorods, pH condition and/or amount of a surfactant are controlled to carry out selective etching and to cause a change in color only by $CN^-$ so that $CN^-$ contained or dissolved in poison samples, water-contaminated environmental samples and legal evidence samples may be detected with ease, and show excellent selectivity, sensitivity and quantitative analyzability to $CN^-$ to provide high usefulness.

Description about National Support Research and Development

This study is conducted by the support of Ministry of Science, ICT and Future Planning, and the subject title is Development of Efficient and Cutting-Edge Analysis Technique and Establishment of On-site Evidence Predictive Factor Data Base (Subject Identification No.: 1711018287).

2. Description of the Related Art

Many cyanide compounds are toxic, because $CN^-$ functions as a reaction inhibitor against cytochrome C oxidase that is an enzyme present in an electron transfer chain in cellular mitochondria. When $CN^-$ is bound with the enzyme, electron transfer from cytochrome C to oxygen is interrupted. As a result, the electron transfer chain is broken and the cell cannot produce ATP any more for energy. The most harmful cyanide compound is an inhalable hydrogen cyanide that exists in a gaseous state at room temperature. Human who eats a solid cyanide compound or cyanide solution in a small amount of 200 mg or inhales 270 ppm of cyanide gas may be dead within 1 minute.

Various detection methods and criteria have been suggested for $CN^-$ in an environmental sample, food or drinking water. The criterion for drinking water is 200 ppb according to EPA of USA and that of Europe is 50 ppb. In addition, the criterion for mineral water is 70 ppb or less. There have been suggested some official methods for analyzing $CN^-$, including titration and spectrometry [US EPA, Titrimetric and manual spectrophotometric determinative methods for cyanide, Method 9014, 1996], potentiometric titration using a cyanide-selective electrode [US EPA, Potentiometric determination of cyanide in aqueous samples and distillates with ion-selective electrode, Method 9213, 1996], flow injection (FI)-amperometry [US EPA, Available cyanide by flow injection, ligand exchange and amperometry, Method OIA-1677, 2004], or the like.

Gold nanorods (AuNRs) are obtained by reducing chlorauric acid hydrate ($HAuCl_4 \cdot H_2O$) with $NaBH_4$ in the presence of cetyltrimethyl ammonium bromide (CTAB) to provide gold nanoparticles and carrying out further reduction with ascorbic acid. Such nanorods have been applied widely in various industrial fields, including sensors, depending on their sizes and shapes.

Nanoparticle colorimetric sensor analysis using a surface plasmon resonance phenomenon of gold nanoparticles theoretically utilizes the principle of inducing free electron vibration of the surface of nanoparticles by the light waves absorbed thereto. Herein, a resonance phenomenon occurs to emit a specific wavelength and shows various colors depending on size, shape and type of the particles. Since gold nanorods (AuNRs) may have a variable color according to a change in dimension of width and length, they may be applied widely to sensors for determining and monitoring a specific material which etchs the nanorods (Chem Soc. Rev. 2013, 42, 2679-2724).

As a metal ion detection colorimetric sensor using gold nanorods known to date, Professor Jiaming Ryu (Jangchow Nomal University, China) has developed a sensor for detecting hexavalent chromium ion ($Cr^{6+}$) by using Cr (VI) ions which can etch gold nanorods selectively [Sensors and Actuators B, 2011, 155, 817-822]. In addition, selective detection of $Cu^{2+}$ ions has been disclosed wherein it uses a change in maximum peak wavelength of UV-Vis spectrum when poly(sodium-4-styrene sulfonate) and polyethylene imine (PEI) are adsorbed to gold nanorods and then bound with $Cu^{2+}$ ions [J. of Colloid and Interface Science 439 (2015) 7-11]. Further, Professor Andres D. Campiglia of Central Florida University, USA has suggested a sensor for analyzing mercury by binding (3-mercaptopropyl) trimethoxysilane to gold nanorods [Talanta 99 (2012) 180-185].

According to the inventors' observations, there is a need for a sensor technology for carrying out rapid detection and analysis of $CN^-$ in environmentally contaminated samples, forensic science samples, drinking water, medicine or industrial sites where chemicals are treated, etc., which may allow real time determination and continuous management, have high stability and enable downsizing.

SUMMARY

The present disclosure is directed to providing a colorimetric detection sensor and a colorimetric detection method of a cyanide anion ($CN^-$) which, by using label-free nanorods having no specific compound bound thereto, may provide high selectivity to a material to be detected, $CN^-$, and allow simple real-time monitoring and quantitative determination with ease even at a very low concentration.

In one aspect of example embodiments, there is provided a colorimetric detection sensor for detecting a cyanide anion ($CN^-$), which includes gold nanorods having an aspect ratio of 0.29-1.

Herein, it is most suitable that the gold nanostructure for detecting a cyanide anion has a rod-like shape. As the difference in dimension between the width and the length becomes bigger, a red shift occurs, resulting in an increase in wavelength. As the difference is decreased, a blue shift occurs, resulting in a decrease in wavelength. The gold nanorods according to the embodiments of the present disclosure have an aspect ratio of 0.29-1, which corresponds to a blue shift, and may show a significant change in color. Therefore, it is the most suitable that the aspect ratio is 0.29-1, since it causes a change in color in a wavelength range of 700 nm-450 nm, particularly the aspect ratio is 0.7-0.8.

According to an example embodiment, the gold nanorods may have a size of 50 nm or less.

According to an example embodiment, in the colorimetric detection sensor, the rod-shaped gold nanorods are etched by $CN^-$ so that they may be changed into a spherical shape, and thus may show a change in color due to a surface resonance phenomenon.

According to an example embodiment, the change in color in the colorimetric detection sensor proceeds from a blue color to a purple color, a pink color or transparency.

According to an example embodiment, the colorimetric detection sensor includes cetyltrimethyl ammonium bromide (CTAB) which is a surfactant at a concentration of 1-3 mM.

According to an example embodiment, the colorimetric detection sensor detects $CN^-$ in a range of pH 6-8, detection at a pH of 6 being particularly advantageous.

According to an example embodiment, the colorimetric detection sensor may detect $CN^-$ at a temperature ranging from room temperature to 50° C.

According to an example embodiment, a detection reaction of $CN^-$ is carried out within 30 minutes.

According to an example embodiment, the concentration of detected $CN^-$ may be judged by the naked eyes, and the change in color of the colorimetric detection sensor may be quantitatively determined by using a spectrophotometer or colorimeter.

In another aspect of example embodiments, there is provided a colorimetric detection method for detecting $CN^-$, which includes: introducing a sample to be detected to a colorimetric detection sensor; and detecting 0.01 ppm or higher of $CN^-$ in the sample to be detected by a change in color of the colorimetric detection sensor, wherein the colorimetric detection sensor includes gold nanorods having an aspect ratio of 0.29-1.

According to an example embodiment, before introducing the sample, the method may further include adjusting pH and temperature of the colorimetric detection sensor to enhance the stability and sensitivity of the nanorods.

According to an example embodiment, the colorimetric detection sensor shows color emission in a wavelength range of 450 nm-700 nm in the introducing, and it shows color emission in a wavelength range of 500 nm-600 nm when $CN^-$ is present in the sample to be detected in the detecting.

According to an example embodiment, the colorimetric sensor may have an absorbance ratio ($A_{538}/A_{679}$) of 0.5-10 in the detecting.

The colorimetric detection sensor for detecting a cyanide anion ($CN^-$) according to the embodiments of the present disclosure has high selectivity to $CN^-$ and has a high sensitivity so as to have a detection limit of 0.01 ppm or less, and thus is very suitable for colorimetric detection. In addition, no interference effect with the other metal cations or anions occurs. As well, the colorimetric detection sensor is convenient to use for a simple determining the content of $CN^-$ on the spot, and requires a short reaction and detection time so that it may be used immediately on the spot. Therefore, the colorimetric detection sensor may be used widely for practical uses in environmentally contaminated samples, forensic science samples, drinking water, medicines, industrial sites where chemicals are treated, or the like.

BRIEF DESCRIPTION OF THE DRAWINGS

The above and other aspects, features and advantages of the disclosed example embodiments will be more apparent from the following detailed description taken in conjunction with the accompanying drawings in which.

DETAILED DESCRIPTION

Example embodiments are described more fully hereinafter. The invention may, however, be embodied in many different forms and should not be construed as limited to the example embodiments set forth herein. Rather, these example embodiments are provided so that this disclosure will be thorough and complete, and will fully convey the scope of the invention to those skilled in the art. In the description, details of features and techniques may be omitted to more clearly disclose example embodiments.

The terminology used herein is for the purpose of describing particular embodiments only and is not intended to be limiting of the invention. As used herein, the singular forms "a," "an" and "the" are intended to include the plural forms as well, unless the context clearly indicates otherwise.

Furthermore, the use of the terms a, an, etc. do not denote a limitation of quantity, but rather denote the presence of at least one of the referenced item. The terms "first," "second," and the like do not imply any particular order, but are included to identify individual elements. Moreover, the use of the terms first, second, etc. do not denote any order or importance, but rather the terms first, second, etc. are used to distinguished one element from another.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

According to example embodiments, the gold nanorods may be obtained as follows. When chlorauric acid hydrate ($HAuCl_4.H_2O$) is reduced with $NaBH_4$ in the presence of cetyltrimethylammonium bromide (CTAB), Au(I) nanoparticle seeds having a size of at most 1.5 nm are produced from Au(III) ions. Then, the nanoparticle seeds are reduced into gold nanorods (AuNRs) with ascorbic acid in the presence of CTAB. Herein, $AgNO_3$ may be added during the reduction to make the gold nanorods with a constant size and shape. The resultant gold nanorods show a surface plasmon resonance phenomenon as like nanoparticles.

According to example embodiments, it is possible to obtain a colorimetric sensor solution optimized for detection of a cyanide anion ($CN^-$) by controlling the aspect ratio of nanorods, pH condition, and/or amount of a surfactant when producing gold nanorods in the above-described method.

Figure 1:
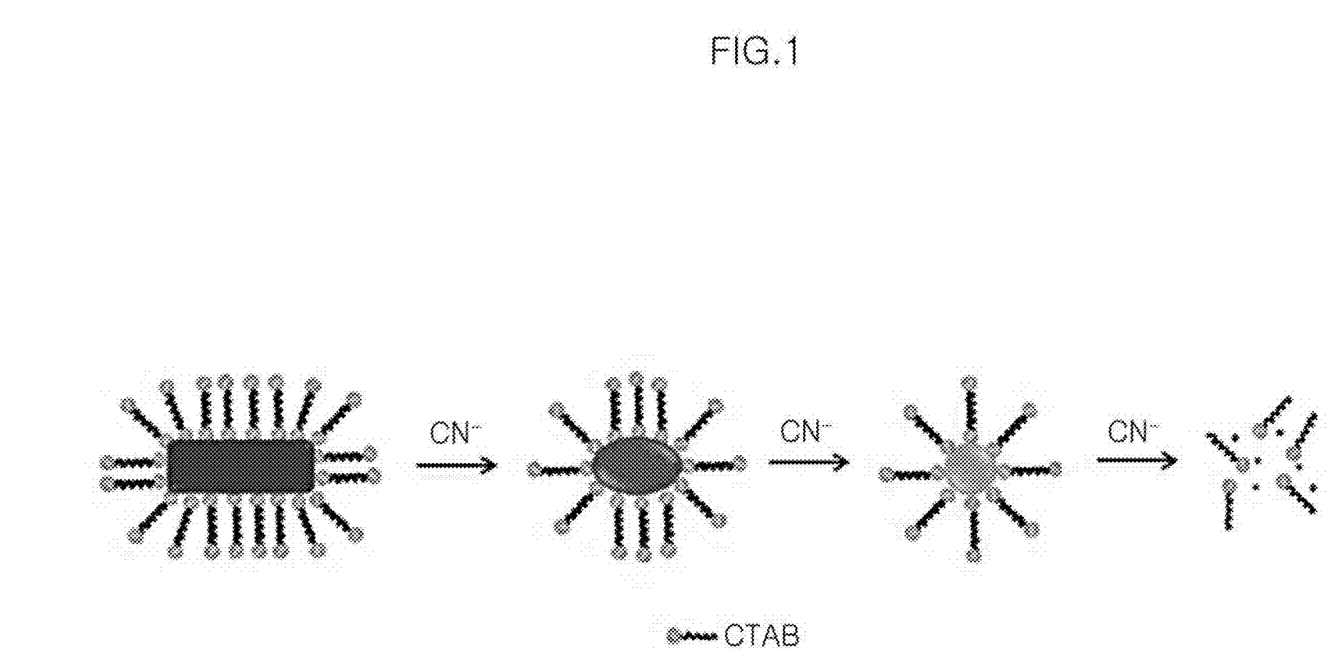
FIG. 1 is a schematic view illustrating the process of etching of gold nanorods with $CN^-$ according to an example embodiment.

FIG. 1 is a schematic view illustrating the process of etching gold nanorods with $CN^-$ according to an example embodiment.

Referring to FIG. 1, when adding a cyanide solution to gold nanorods surrounded with CTAB which is a surfactant, etching starts from the axial direction (i.e., the side having a shorter length) of nanorods by $CN^-$, and thereby the rod-like shape is changed into an elliptical shape and then a spherical shape, and the gold nanorods are finally dissolved in the solution.

Herein, the color of the colorimetric sensor solution is changed, depending on etching degree, from a blue color to a purple, pink and a light pink color in turn with time, and finally becomes transparent.

Such a change in color is caused by the surface resonance phenomenon of the nanoparticles. The degree of a change in shape of the nanorods varies with the amount of $CN^-$. For example, when $CN^-$ concentration is low, the nanorods are changed into an elliptical shape and do not undergo further etching reaction and a change in shape any longer.

The examples and experiments will now be described. It is intended that the present disclosure not be limited to the particular example embodiments disclosed, but that the present disclosure will include all embodiments, including modifications, equivalents and substitutes, falling within the scope of the appended claims.

Preparation Example 1: Preparation of Gold Nanorods

To 7.5 mL of 0.1 M CTAB, 0.25 mL of 0.01M $HAuCl_4$ is added and the resultant mixture is agitated and stored with ice. To the mixture, 0.6 mL of 0.01M $NaBH_4$ is added and mixed for 2 minutes, and the resultant mixture is stored at room temperature for 2 hours. At that time, the solution undergoes a change in color from a yellow color to a dark yellow color, and then to a light brown color. The resultant solution is used as a seed solution for forming nanorods.

Then, 0.2 mL of 10 mM $AgNO_3$, 12 mL of 50 mM $HAuCl_4$ and 95 mL of 0.1M CTAB are mixed at room temperature. To the resultant mixture, 0.48 mL of 0.2M ascorbic acid and 0.2 mL of the seed solution are added, and the mixture is allowed to stand for 20 minutes.

Figure 2:
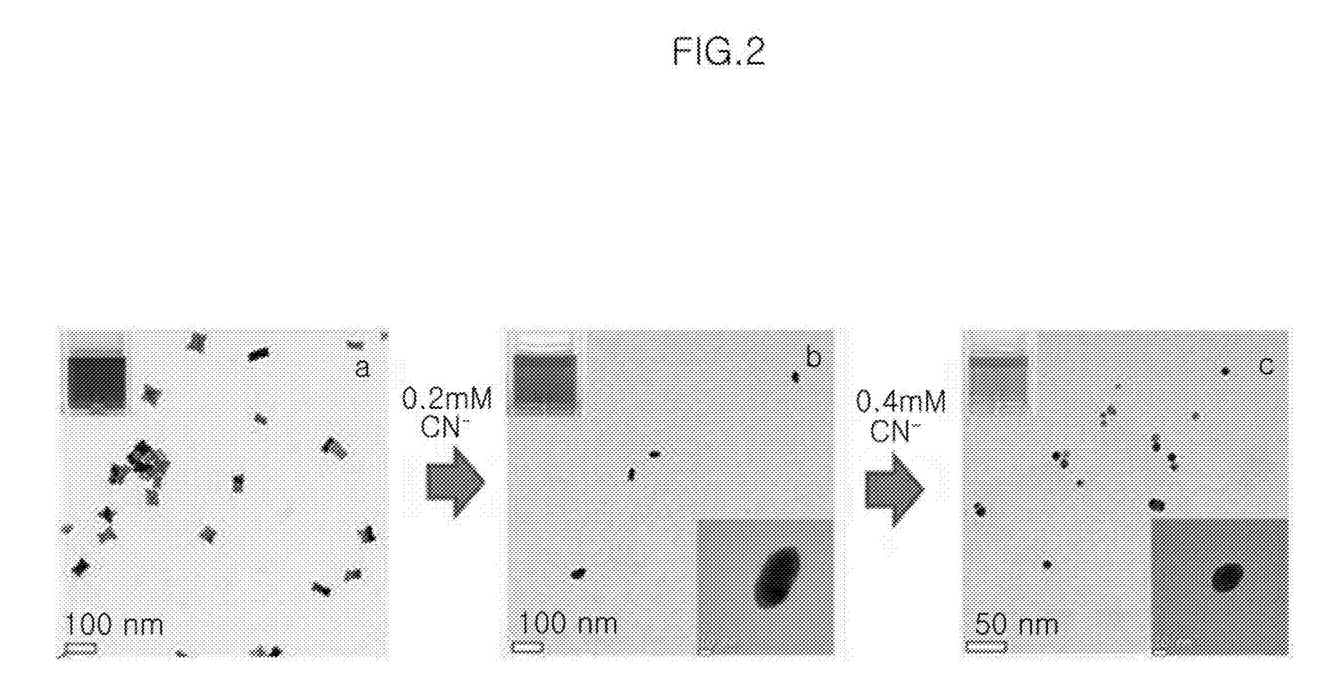
FIG. 2 is a transmission electron microscopic (TEM) image (portion (a)) of gold nanorods, TEM image (portion (b)) of modified gold nanorods in the presence of 0.2 mM $CN^-$, and TEM image (portion (c)) of modified gold nanorods in the presence of 0.4 mM $CN^-$ according to an example.

The photographic image of the resultant colorimetric sensor solution and TEM image of gold nanorods are shown in portion (a) of FIG. 2. The resultant gold nanorods have a size of at most 50 nm at the width and length. The solution has a dark blue color due to the surface resonance phenomenon of the nanorods.

Change in Color Caused by $CN^-$

To the colorimetric sensor solution prepared in the above Preparation Example 1, $CN^-$ is added to a concentration of 0.2 mM. The photographic image of the resultant colorimetric sensor solution and TEM image of gold nanorods are shown in portion (b) of FIG. 2.

$CN^-$ is further added to the solution to a concentration of 0.4 mM. The photographic image of the resultant colorimetric sensor solution and TEM image of gold nanorods are shown in portion (c) of FIG. 2.

Referring to FIG. 2, the nanorods prepared in the Preparation Example 1 is etched after the addition of $CN^-$, so that they are changed into an elliptical shape, and after $CN^-$ is further added, they are changed into a spherical shape.

Reactivity of Gold Nanoparticles Depending on Amount of CTAB

Figure 3A:
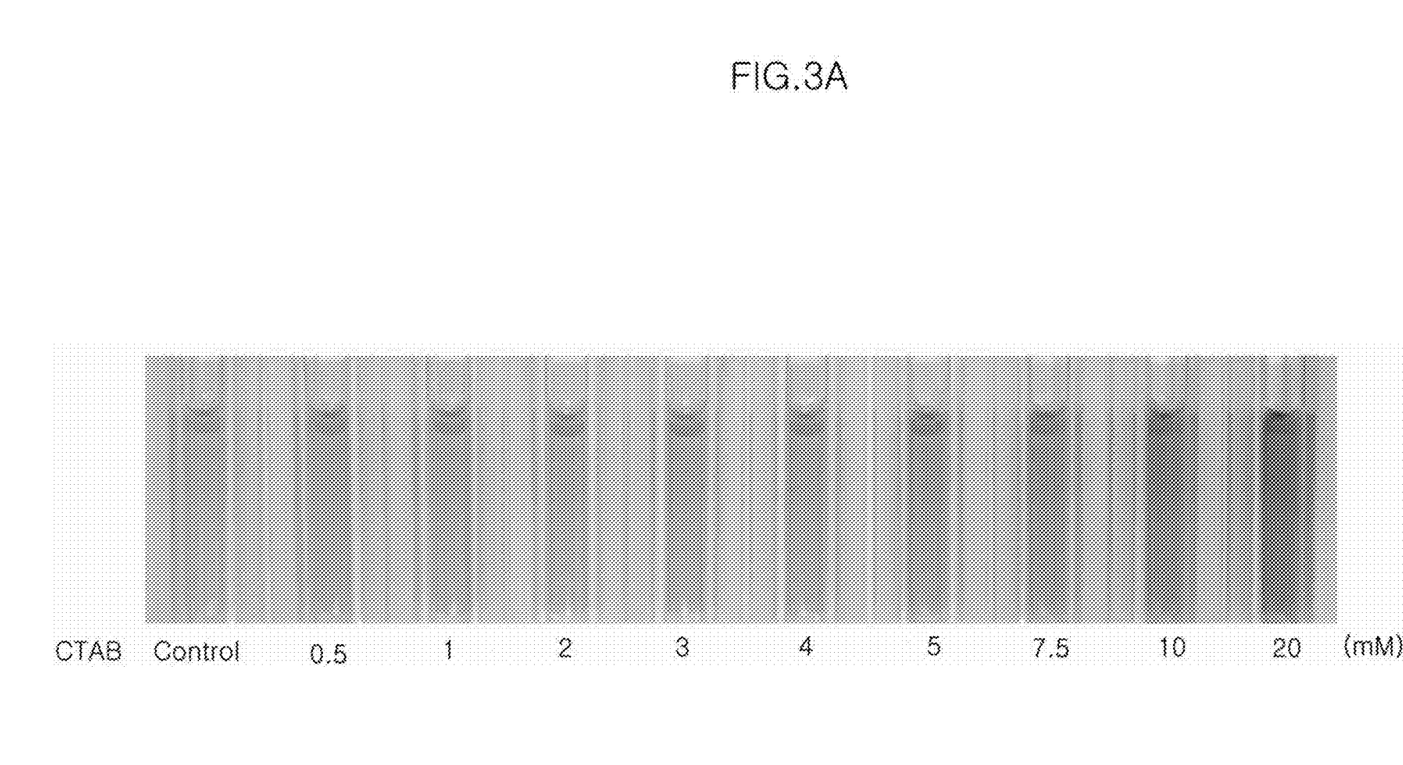
FIG. 3A is an image illustrating a change in color of a colorimetric sensor solution depending on CTAB concentration after adding $CN^-$ in Example 2.

A colorimetric sensor solution is prepared in the same manner as the Preparation Example 1, except that the amount of CTAB is changed into 0 (control), 0.5, 1, 2, 3, 4, 5, 7.5, 10 and 20 mM. To each colorimetric sensor solution, $CN^-$ is added to a concentration of 0.35 mM and a reaction is carried out. FIG. 3A is a photographic image illustrating a change in color after the reaction.

As can be seen from FIG. 3A, when CTAB is added in an amount of 0-5 mM, etching of gold nanorods proceeds and the nanorods undergo a change in color from a blue color to a purple color. On the contrary, when CTAB is added in an amount of 20 mM, a blue color similar to the color of gold nanorods is observed, suggesting that etching is not carried out much. This is because CTAB surrounds the gold nanorods in most part thereof, and thus $CN^-$ etching cannot occur with ease even at the side of longitudinal direction as well as the side of axial direction. However, when the amount of the surfactant CTAB is low in the side of axial direction of the nanorods as shown in FIG. 1, contact with $CN^-$ occurs with ease.

Figure 3B:
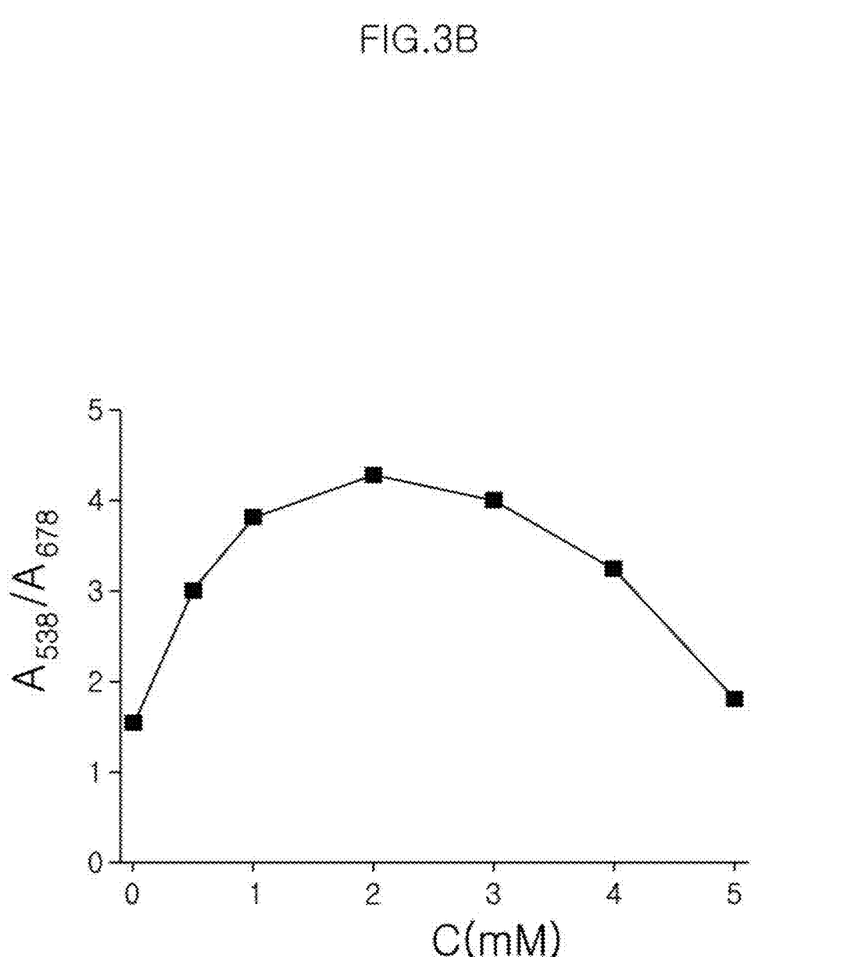
FIG. 3B is an image illustrating an absorbance ratio ($A_{538}/A_{678}$) of a colorimetric sensor solution depending on CTAB concentration after adding $CN^-$ in Example 2.

FIG. 3B shows an absorbance ratio ($A_{538}/A_{678}$) depending on CTAB concentration in a range of CTAB concentration of 0-5 mM. Referring to FIG. 3B, the highest absorbance ratio appears at a CTAB concentration of 2 mM, which means the optimum reactivity.

Reactivity of Gold Nanoparticles Depending on pH

Samples having a pH of 1-13 are prepared by adjusting pH of the colorimetric sensor solution obtained in the Preparation Example 1. To adjust pH, 1M HCl and 1M NaOH are used. Then, $CN^-$ is added to each sample to a concentration of 0.35 mM. The photographic image of each sample is shown in FIG. 4A and the graph of absorbance ratio ($A_{538}/A_{678}$) determined by UV-Vis spectrometry is shown in FIG. 4B.

Figure 4A:
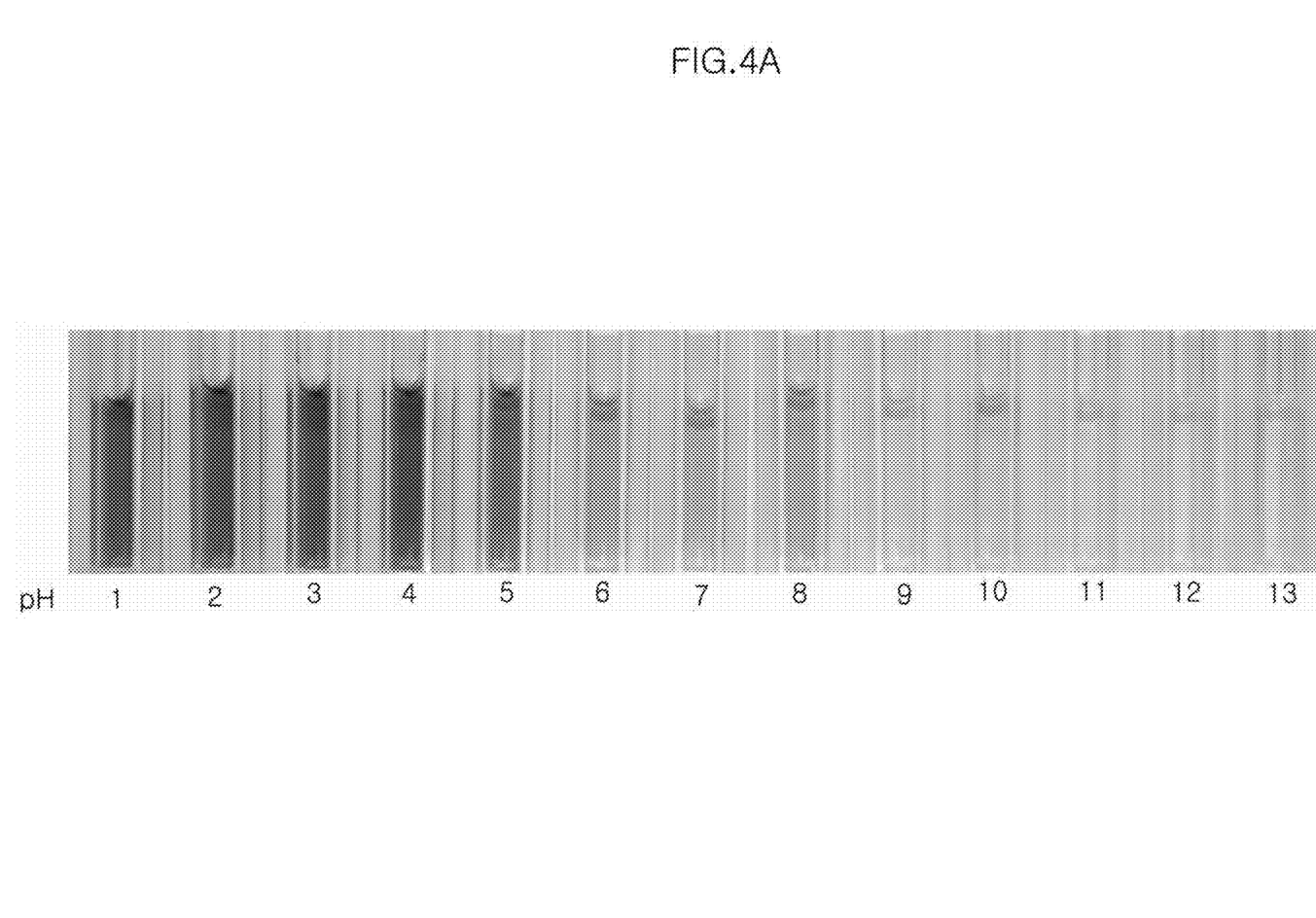
FIG. 4A is an image illustrating a change in color of a colorimetric sensor solution depending on a change in pH in Example 3.

Referring to FIG. 4A, little change in color occurs at pH 4 or lower, which suggests that $CN^-$ does not react with gold nanorods. The reaction starts from pH 5 and a pink color is observed at pH 6-8, suggesting that the gold nanorods have a spherical shape.

Figure 4B:
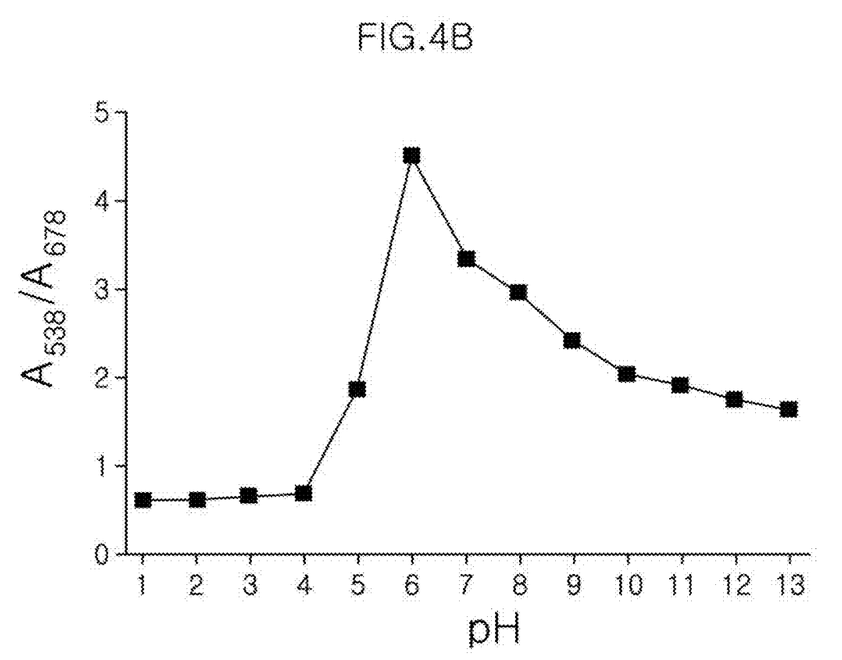
FIG. 4B is a graph illustrating an absorbance ratio ($A_{538}/A_{678}$) of a colorimetric sensor solution depending on a change in pH in Example 3.

Referring to the absorbance graph of FIG. 4B, the highest absorbance appears at pH 6 and then the absorbance is decreased gradually from pH 6. It can be seen from the above results that the colorimetric sensor solution shows the strongest reactivity at pH 6.

Reactivity of Gold Nanoparticles Depending on Reaction Temperature

After pH of the colorimetric sensor solution obtained in the Preparation Example 1 is adjusted to 6, six samples are prepared at a different temperature of 25° C. (room temperature), 30, 35, 40, 45 and 50° C. Then, $CN^-$ is added to each sample to a concentration of 0.35 mM, each sample is allowed to react for 25 minutes while maintaining the temperature, and then a change in color is observed. The absorbance ratio ($A_{538}/A_{678}$) of each sample is shown in FIG. 5.

After observing a change in color, it can be seen that the change in color as shown in FIG. 1 proceeds more rapidly, as the reaction temperature increases.

Figure 5:
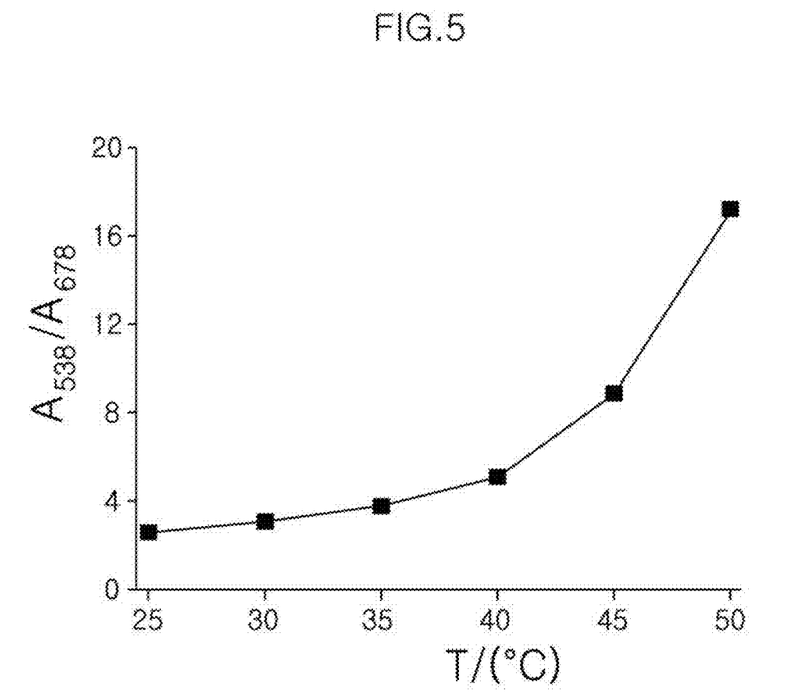
FIG. 5 is a graph illustrating an absorbance ratio ($A_{538}/A_{678}$) of a colorimetric sensor solution depending on reaction temperature after adding $CN^-$ in Example 4.

Referring to FIG. 5, a change in absorbance ratio at a temperature of 25-40° C. is not big but the absorbance ratio increases at 40° C. or higher. This is because the reactivity between nanorod particles and $CN^-$ increases. Therefore, it can be seen that a temperature of 40° C. or higher is suitable for increasing the reactivity between nanorods and $CN^-$. In addition, since the absorbance ratio is 2.55 at 25° C. (room temperature) but the absorbance is 17.233 at 50° C., it can be seen that the reactivity at 50° C. is at least 6 times higher than the reactivity at room temperature. Therefore, in the example embodiments, it is possible to increase the reaction temperature adequately, if necessary for rapid detection of $CN^-$.

Reaction Time Depending on $CN^-$ Concentration

The colorimetric sensor solution obtained in the Preparation Example 1 is adjusted to pH 6 and reaction is carried out at room temperature. After adding $CN^-$ to four samples to a concentration of 0.1, 0.2, 0.3 and 0.4 mM, the absorbance ratio ($A_{538}/A_{678}$) is measured continuously with time and the results are shown in FIG. 6.

Figure 6:
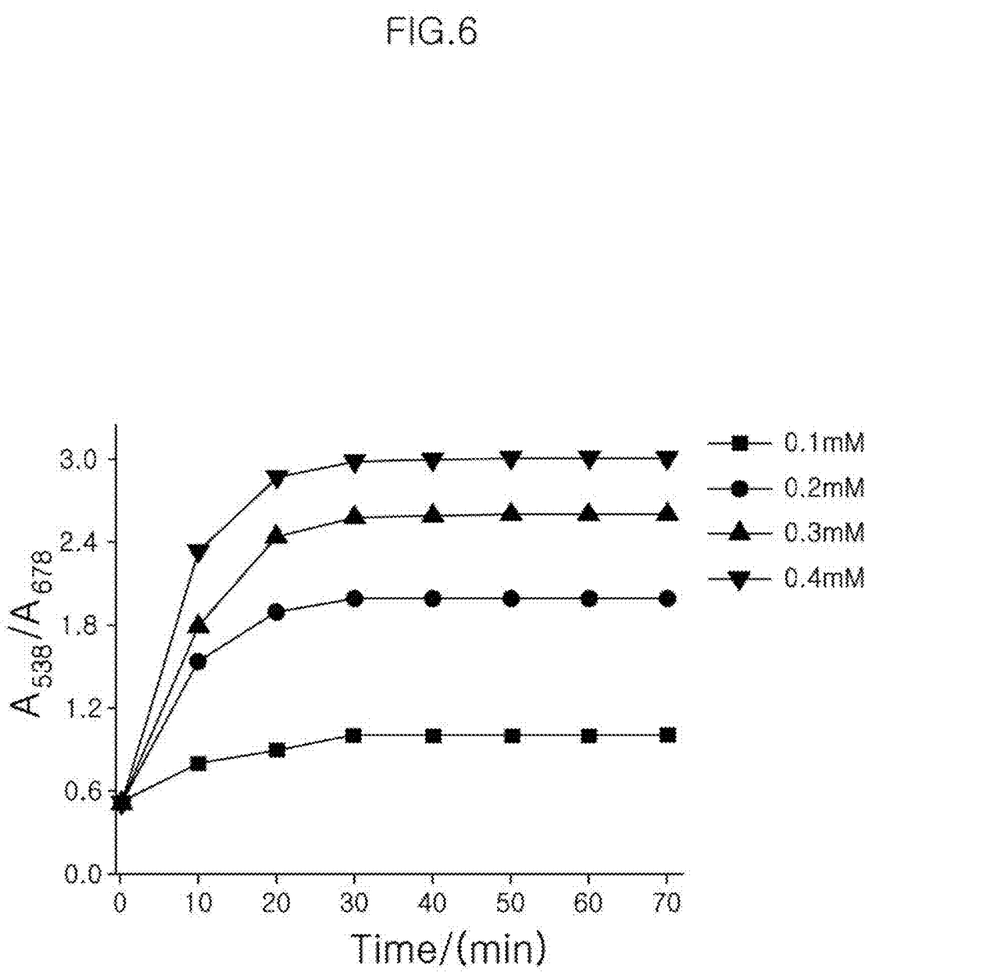
FIG. 6 is a graph illustrating an absorbance ratio ($A_{538}/A_{678}$) of a colorimetric sensor solution with time depending on $CN^-$ concentration in Example 5.

Referring to FIG. 6, the absorbance increases rapidly by the time of 20 minutes at all concentrations of $CN^-$ and then increases gradually between 20 minutes and 30 minutes. Then, it can be seen that little reaction occurs from 30 minutes. Therefore, it is thought that under the above-mentioned condition, the reaction between gold nanorods and $CN^-$ is completed by the time of about 30 minutes, and the optimum time for $CN^-$ detection is 30 minutes.

Selectivity of Colorimetric Sensor Solution to Various Ions

Figure 7A:
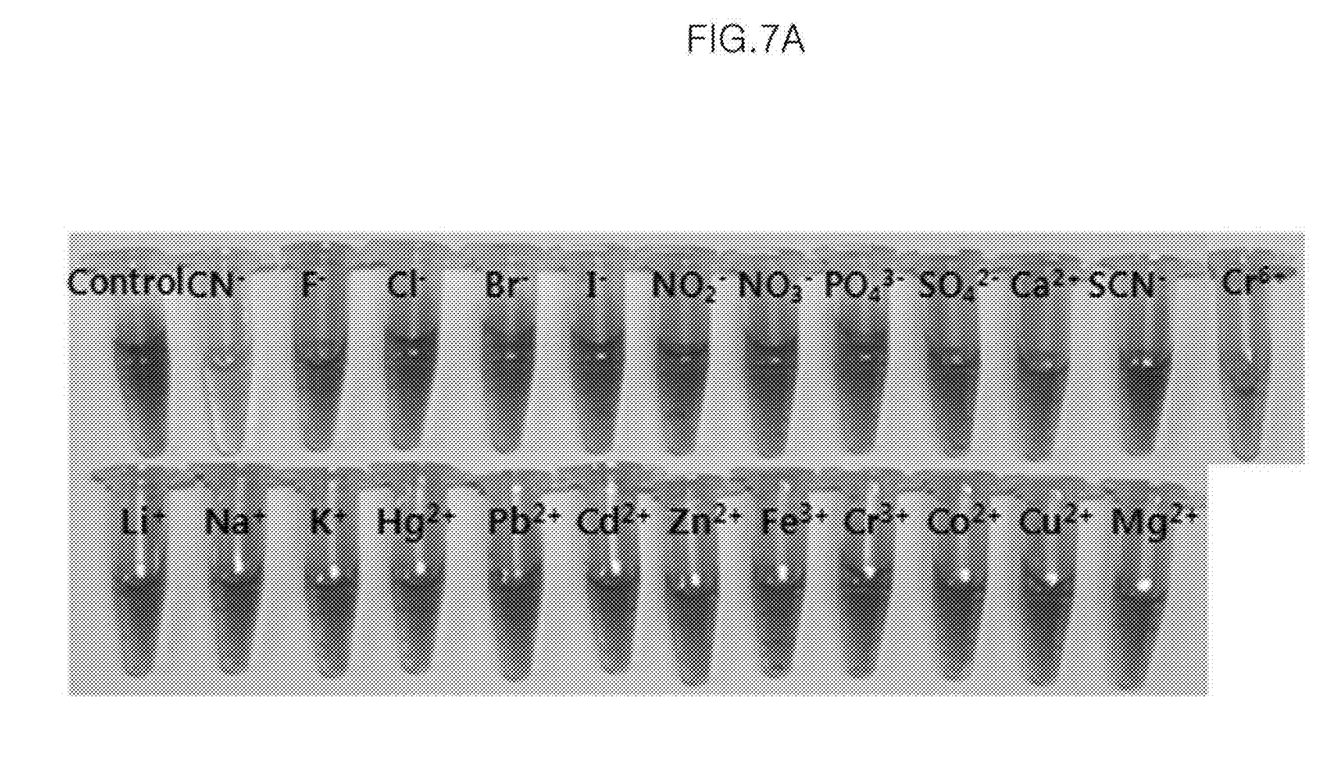
FIG. 7A is an image illustrating a change in color of a colorimetric sensor solution, when adding various anions and metal ions in Example 6.

The colorimetric sensor solution obtained in the Preparation Example 1 is adjusted to pH 6. To the colorimetric sensor solution at room temperature, 10 types of anions ($CN^-$, $F^-$, $Cl^-$, $Br^-$, $I^-$, $NO_2^-$, $NO_3^-$, $PO_4^{3-}$, $SO_4^{2-}$, $SCN^-$) and 14 types of cations ($Ca^{2+}$, $Cr^{6+}$, $Li^+$, $Na^+$, $K^+$, $Hg^{2+}$, $Pb^{2+}$, $Cd^{2+}$, $Zn^{2+}$, $Fe^{3+}$, $Cr^{3+}$, $Co^{2+}$, $Cu^{2+}$, $Mg^{2+}$) are added and reaction is carried out for 30 minutes, and then a change in color is observed. FIG. 7A is a photographic image of each sample after the reaction, FIGS. 7B and 7C are UV-Vis spectrum of each sample, and FIG. 7D is a graph of absorbance ratio ($A_{538}/A_{678}$).

In FIG. 7A, the colorimetric sensor solution to which $CN^-$ is added is changed into a pink color, which is significantly different from the colorimetric sensor solutions to which different anions and metal ions are added. This means that etching of gold nanorods occurs only by $CN^-$.

Figure 7B:
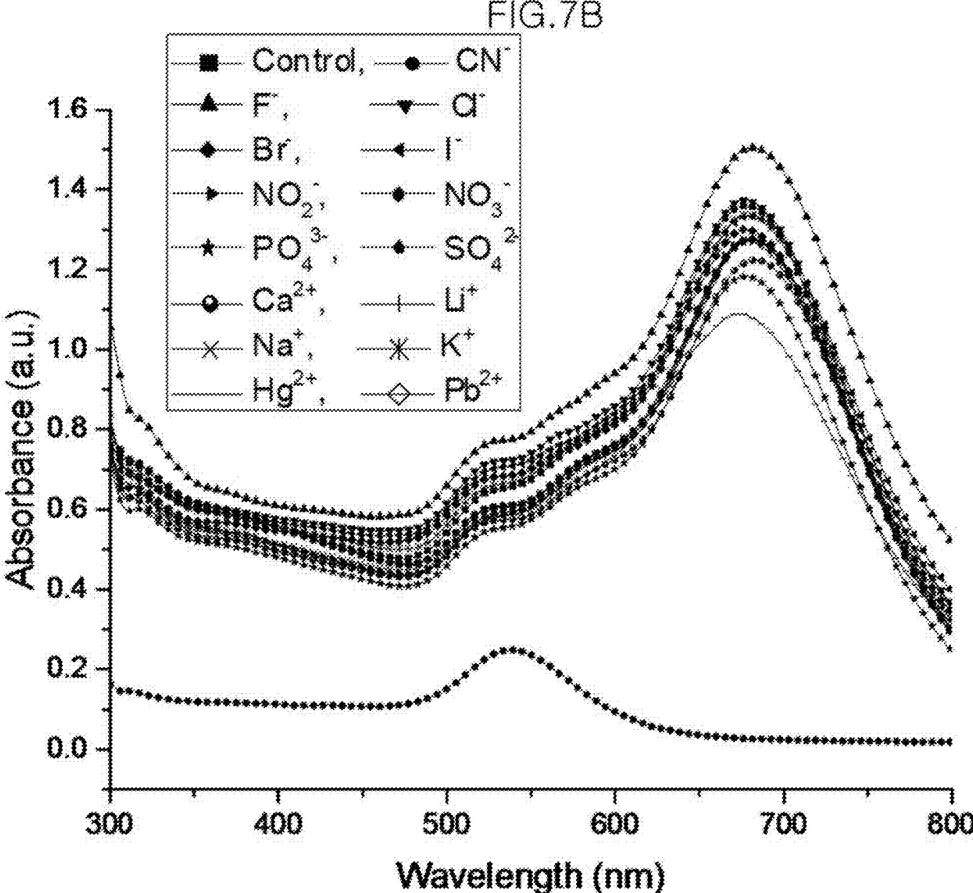
FIGS. 7B and 7C are an image illustrating absorption spectra of a colorimetric sensor solution, when adding various anions and metal ions in Example 6.
Figure 7C:
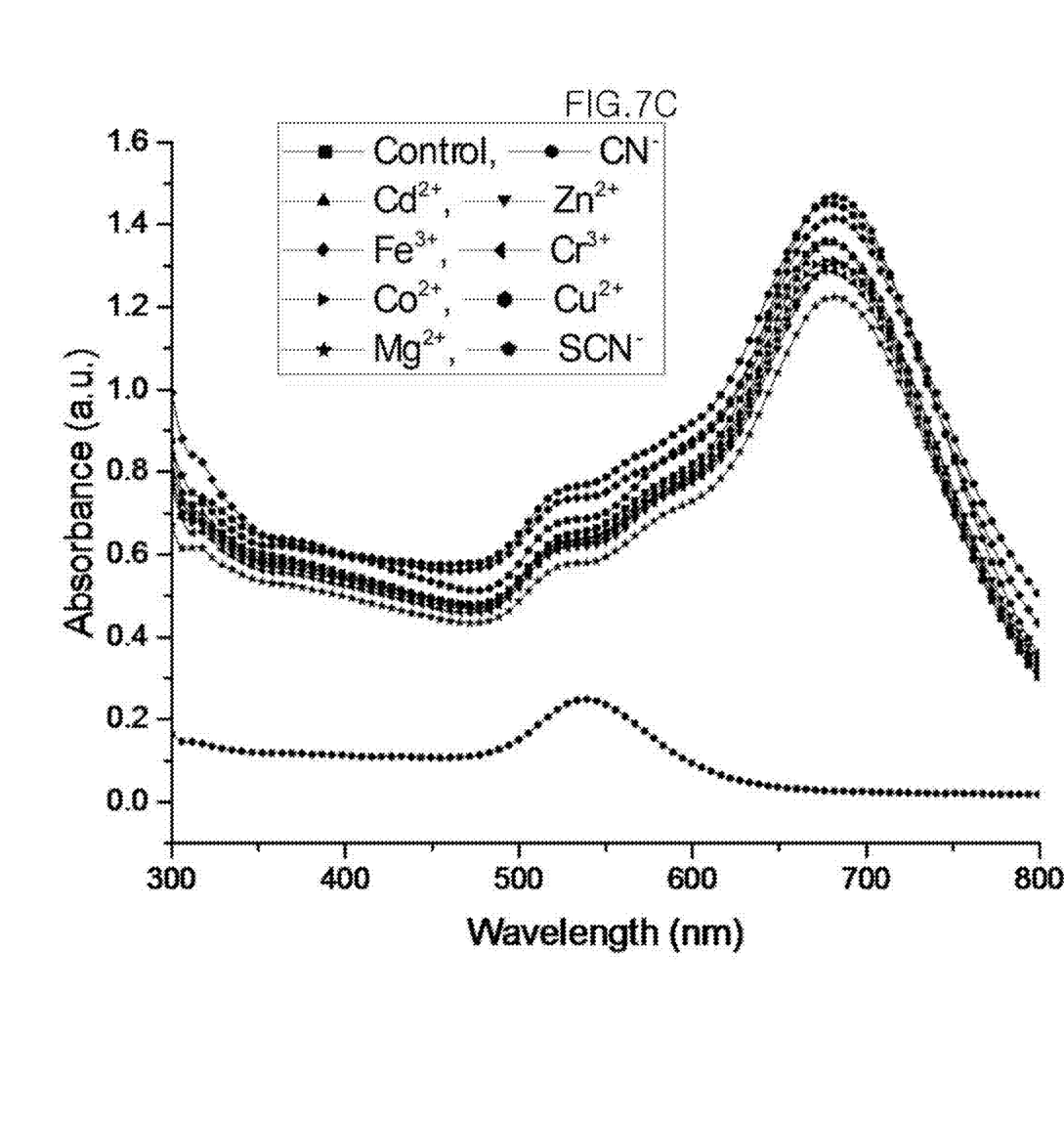

In FIGS. 7B and 7C, the solutions to which different ions are added show absorbance spectra very similar to the absorbance spectrum of the colorimetric sensor solution, have absorption peaks at 524 nm, 584 nm and 680 nm, and show a very strong absorbance at 680 nm (blue). On the contrary, the solution to which $CN^-$ is added has no absorption peak at 680 nm and has an absorption peak at 538 nm (pink).

Figure 7D:
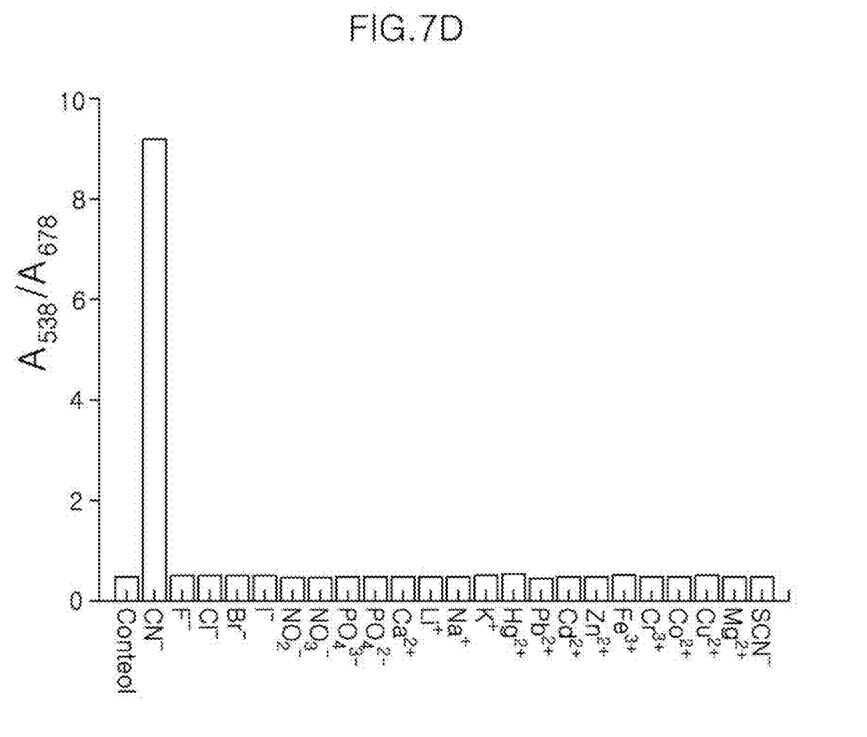
FIG. 7D is a graph illustrating an absorbance ratio ($A_{538}/A_{678}$) of a colorimetric sensor solution, when adding various anions and metal ions in Example 6.

FIG. 7D shows spectrum of each sample in terms of an absorbance ratio. Unlike the other samples, the solution to which $CN^-$ is added shows an absorbance ratio at least 20 times higher as compared to the other samples. Such a high absorbance ratio means excellent selectivity to $CN^-$.

Sensitivity and Calibration Curve of Colorimetric Sensor Solution

The colorimetric sensor solution obtained in the Preparation Example 1 is adjusted to pH 6, $CN^-$ is added to a concentration of 0.1, 0.2. 0.3 and 0.4 mM, and reaction is carried out at room temperature for 30 minutes.

Figure 8A:
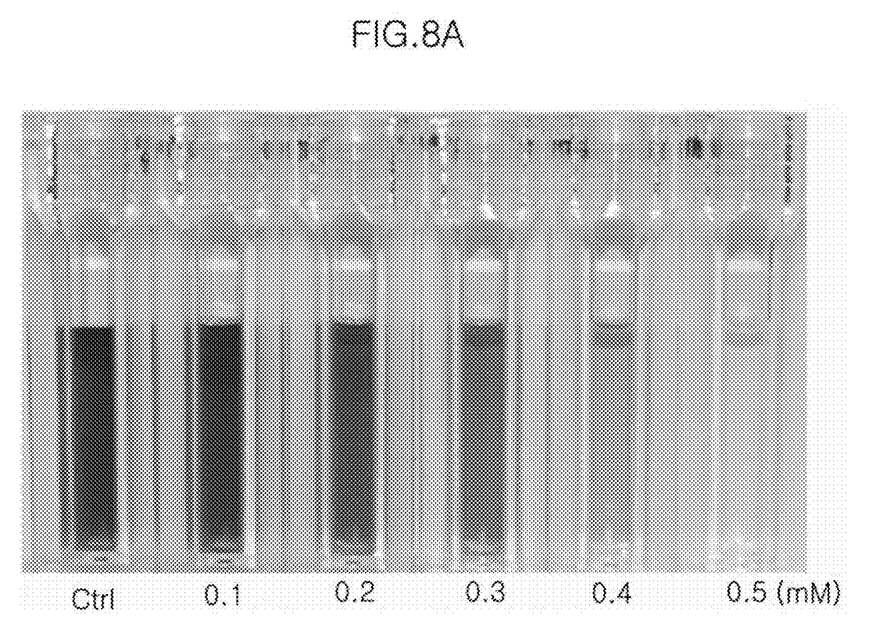
FIG. 8A is an image illustrating a change in color of a colorimetric sensor solution depending on $CN^-$ concentration in Example 7.
Figure 8B:
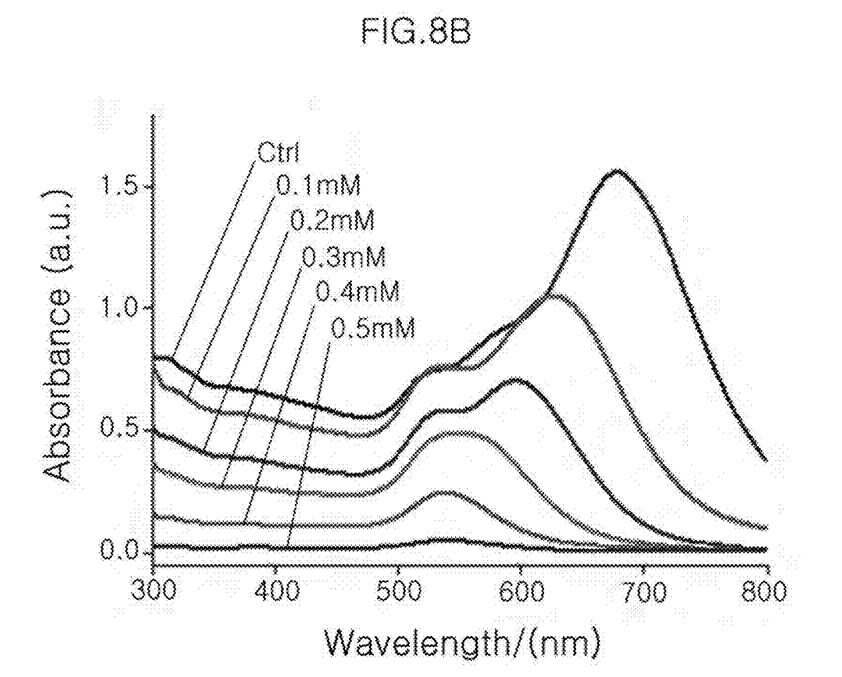
FIG. 8B is an absorption spectrum of a colorimetric sensor solution depending on $CN^-$ concentration in Example 7.
Figure 8C:
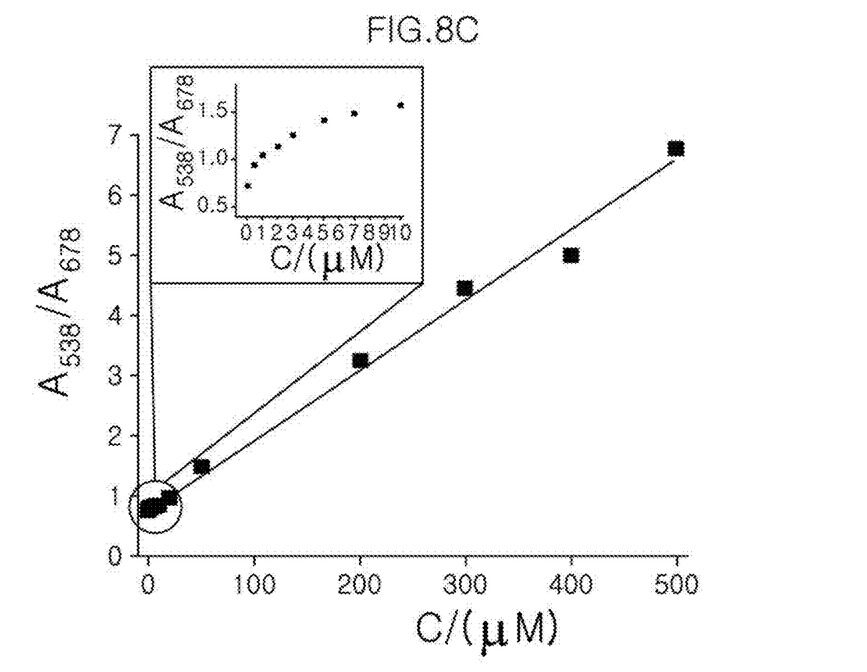
FIG. 8C is a calibration curve illustrating an absorbance ratio ($A_{538}/A_{678}$) of a colorimetric sensor solution depending on $CN^-$ concentration in Example 7.

FIG. 8A is a photographic image illustrating a change in color depending on $CN^-$ concentration and FIG. 8B is an absorption spectrum depending on $CN^-$ concentration. FIG. 8C is a calibration curve of absorbance ratio ($A_{538}/A_{678}$) and provides excellent results with a linear calibration equation of y=0.01172x+0.7538 and an absorption coefficient ($r^2$) of 0.99182. The following Table 1 shows the values in the graph of FIG. 8C in more detail.

TABLE 1

| Equation | Y = a + b*x | — | — |
|---|---|---|---|
| Weight | instrumental | — | — |
| Residual sum of squares (RSS) | 0.81538 | — | — |
| Pearson's r | 0.99631 | — | — |
| Adj. R-Square | 0.99182 | — | — |
| — | — | Value | Standard error |
| B | Intercept | 0.7538 | 0.07473 |
|   | Slope | 0.01172 | 3.36394 × 10$^{-4}$ |

Figure 8D:
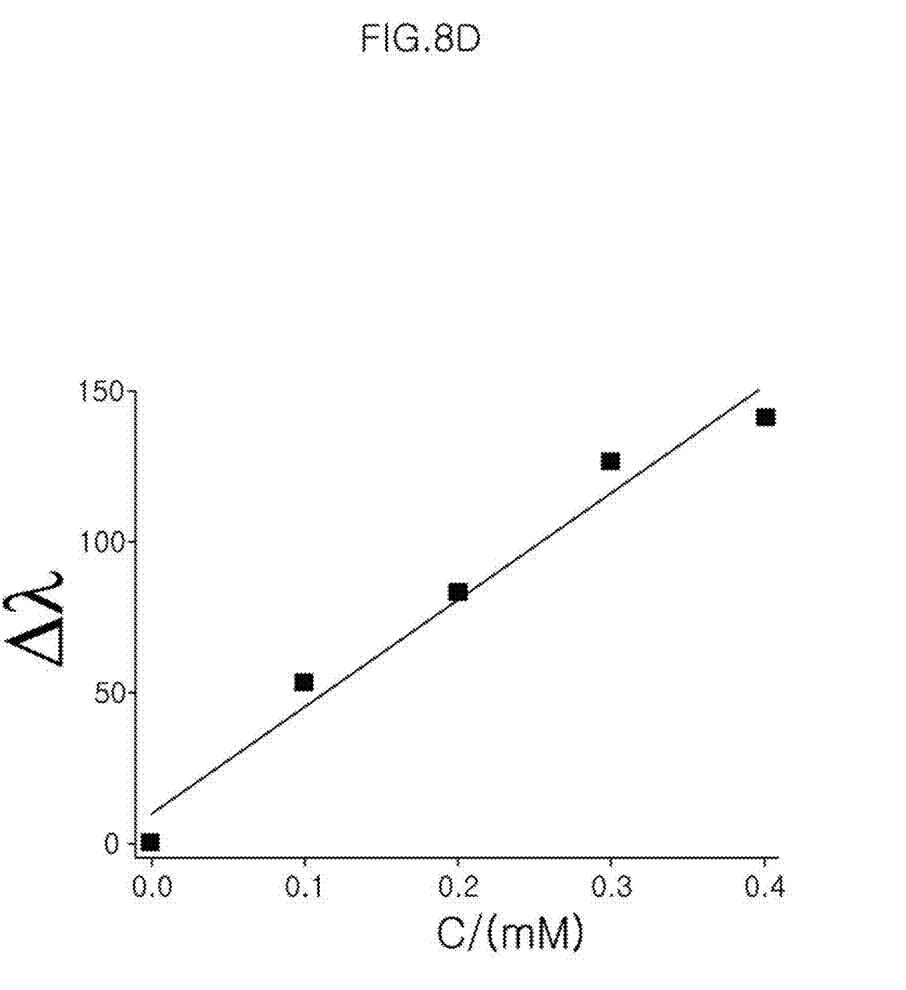
FIG. 8D is a calibration curve illustrating a difference in maximum absorbance (AA) of a colorimetric sensor solution depending on $CN^-$ concentration in Example 7.

FIG. 8D is a calibration curve of the difference (Δλ) between the maximum absorbance of the colorimetric sensor solution (control) and the maximum absorbance of each sample having a different concentration. The maximum absorbance difference (Δλ) depending on $CN^-$ is 0-140 nm, and excellent results are obtained with a linear calibration equation of y=355x+9.6 and an absorption coefficient ($r^2$) of 0.9619. The following Table 2 shows the detailed values regarding the graph of FIG. 8D.

TABLE 2

| Equation | Y = a + b*x | — | — |
|---|---|---|---|
| Weight | instrumental | — | — |

TABLE 2-continued

| | | Value | Standard error |
|---|---|---|---|
| Residual sum of squares (RSS) | 370 | — | — |
| Pearson's r | 0.98561 | — | — |
| Adj. R-Square | 0.9619 | — | — |
| — | — | Value | Standard error |
| B | Intercept | 9.6 | 8.61046 |
| | Slope | 355 | 35.152 |

Evaluation of Effectiveness of Colorimetric Sensor Solution

To carry out a test of $CN^-$ detection in mineral water, commercially available mineral water is purchased and is determined whether it contains $CN^-$ or not. Then, validation is carried out according to the present disclosure and mineral water free from $CN^-$ after the determination is used as a blank sample.

To a blank sample, $CN^-$ is added to 0.1 and 0.3 mM to provide samples. Then, the absorbance of each sample is determined by UV-Vis spectrometry and the calibration curve prepared in Example 7 is used to determine the detected amount, coefficient of variation (CV) and recovery (%). The results are shown in the following Table 3.

TABLE 3

| $CN^-$ addition (mM) | Detected concentration (mM) | CV (Coefficient of Variation) | Recovery (%) | Limit of Detection (nM) |
|---|---|---|---|---|
| 0.1 | 0.1024 ± 0.0035 | 0.0349 | 102.4 ± 3.577 | 0.5 |
| 0.3 | 0.302 ± 0.0052 | 0.0171 | 100.9 ± 1.731 | |

As shown in Table 3, the limit of detection (LOD) of $CN^-$ using the colorimetric sensor solution according to the example embodiments is 0.5 nM. In the samples to which $CN^-$ is added to a concentration of 0.1 and 0.3 mM, the detected amounts are 0.1024±0.0035 and 0.302±0.0052, respectively, which very nearly approach the actual addition amounts. In addition, excellent coefficients of variation of 0.0349 and 0.0171 are obtained along with high recovery ratios of 102.4±3.577 and 100.9±1.731. In general, there have been many hindrance factors in real-time on-site detection of $CN^-$ in products with various compositions, such as environmentally contaminated samples, forensic science samples, drinking water, medicines or industrial sites where chemicals are treated, etc. However, the colorimetric sensor solution including gold nanorods according to the example embodiments of the present disclosure shows excellent performance and has high selectivity.

While the example embodiments have been shown and described, many modifications can be made to adapt a particular situation or material to the teachings of the present disclosure without departing from the essential scope thereof. Therefore, it is intended that the present disclosure not be limited to the particular example embodiments disclosed herein, but that the present disclosure will include all embodiments falling within the scope of the appended claims.

What is claimed is:

1. A colorimetric detection sensor for detecting a cyanide anion (CN—), comprising a colorimetric sensor solution comprising gold nanorods having an aspect ratio of 0.29, wherein the gold nanorods are rod-shaped and are etched by CN— so that the rod-shaped gold nanorods are adapted to change into a spherical shape, and thereby are configured to produce a change in color due to a surface resonance phenomenon, and wherein the colorimetric sensor solution comprises cetyltrimethylammonium bromide (CTAB), which is a surfactant, at a concentration of 1-3 mM.

2. The colorimetric detection sensor according to claim 1, wherein the aspect ratio of the gold nanorods is 0.7-0.8.

3. The colorimetric detection sensor according to claim 1, wherein the gold nanorods have widths and lengths of 50 nm or less, respectively.

4. The colorimetric detection sensor according to claim 1, wherein the color of the colorimetric detection sensor changes from a blue color to a purple color, a pink color or transparency.

5. The colorimetric detection sensor according to claim 1, wherein the colorimetric detection sensor detects $CN^-$ in a range of pH 6-8.

6. The colorimetric detection sensor according to claim 1, wherein the colorimetric detection sensor detects $CN^-$ at pH 6.

7. The colorimetric detection sensor according to claim 1, wherein the colorimetric detection sensor detects $CN^-$ at a temperature ranging from room temperature to 50° C.

8. The colorimetric detection sensor according to claim 1, wherein a detection reaction of $CN^-$ is carried out within 30 minutes.

9. The colorimetric detection sensor according to claim 1, wherein a concentration of detected $CN^-$ is quantitatively determined by measuring a change in color of the colorimetric detection sensor with a spectrophotometer or colorimeter.

10. A colorimetric detection method for detecting $CN^-$, which comprises:
    introducing a sample to be detected to a colorimetric detection sensor according to claim 1; and
    detecting 0.01 ppm or higher of $CN^-$ in the sample to be detected by a change in color of the colorimetric detection sensor,
    wherein the colorimetric detection sensor includes gold nanorods having an aspect ratio of 0.29-1.

11. The colorimetric detection method according to claim 10, which further comprises, before introducing the sample, adjusting pH and temperature of the colorimetric detection sensor to enhance stability and sensitivity of the nanorods.

12. The colorimetric detection method according to claim 10, wherein the colorimetric detection sensor shows color emission in a wavelength range of 450 nm-700 nm in the introducing, and shows color emission in a wavelength range of 500 nm-600 nm when $CN^-$ is present in the sample to be detected in the detecting.

13. The colorimetric detection method according to claim 10, wherein the colorimetric sensor has an absorbance ratio ($A_{538}/A_{679}$) of 0.5-10 in the detecting.

* * * * *